United States Patent [19]

Debono

[11] Patent Number: 4,497,802

[45] Date of Patent: Feb. 5, 1985

[54] N-ACYL GLYCOPEPTIDE DERIVATIVES

[75] Inventor: Manuel Debono, Indianapolis, Ind.

[73] Assignee: Eli Lilly and Company, Indianapolis, Ind.

[21] Appl. No.: 544,336

[22] Filed: Oct. 21, 1983

[51] Int. Cl.³ .................... A61K 37/00; C07C 103/52; A61K 35/00

[52] U.S. Cl. ................ 514/8; 260/112.5 R; 424/118

[58] Field of Search ................. 260/112.5 R; 424/118, 424/177

[56] References Cited

U.S. PATENT DOCUMENTS

| | | | |
|---|---|---|---|
| 2,990,329 | 6/1961 | Philip et al. | 167/65 |
| 3,928,571 | 12/1975 | Raun | 424/118 |
| 4,029,769 | 6/1977 | Debono | 424/118 |
| 4,115,552 | 9/1978 | Hamill et al. | 424/118 |
| 4,122,168 | 10/1978 | Michel et al. | 424/118 |
| 4,322,343 | 3/1982 | Debono | 260/112.5 R |
| 4,322,406 | 3/1982 | Debono et al. | 424/118 |

OTHER PUBLICATIONS

D. H. Williams et al., "Structure of the Antibiotic Ristocetin A," J. C. S. Chem. Comm. 1979, 906-908.

*Primary Examiner*—Delbert R. Phillips
*Attorney, Agent, or Firm*—Nanch J. Harrison; Arthur R. Whale

[57] ABSTRACT

N-Acyl-glycopeptide antibiotics having the formula

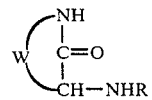

and their salts are useful new antibiotics. The N-acyl actaplanin derivatives also increase feed-utilization efficiency and promote growth in animals and improve milk production in lactating ruminants.

38 Claims, No Drawings

N-ACYL GLYCOPEPTIDE DERIVATIVES

SUMMARY OF THE INVENTION

This invention provides a new group of N-acylated glycopeptide antibiotics. The derivatives of this invention are active against gram-positive microorganisms. Certain of the derivatives enhance feed-utilization efficiency and promote growth in ruminants, swine and poultry and improve milk production in lactating ruminants.

DETAILED DESCRIPTION

The glycopeptide derivatives of this invention are represented by the formula 1:

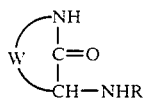
  1 wherein W is the remaining portion of a glycopeptide antiobiotic selected from A35512 factors A, B, C, E and H, A35512B pseudoaglycone, A41030 factors A, B, C, D, E, F and G, A47934, ristocetin A, ristocetin A pseudoaglycone, actaplanin factors A, $B_1$, $B_2$, $B_3$, $C_{1a}$, $C_{2a}$, $C_3$, $D_1$, $D_2$, $E_1$, G, K, L, M, N and O and actaptanin pseudoaglycone which have the common structural formula 2:

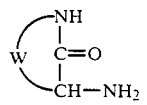
  2 and R is an acyl group selected from:

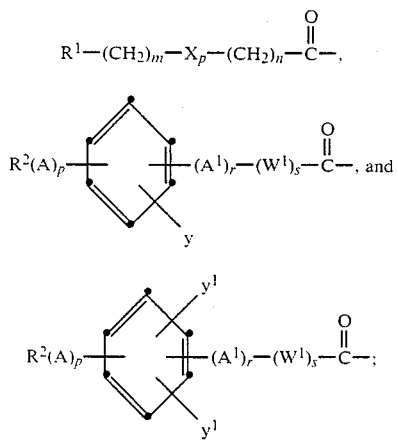

p, r and s are 0 or 1; m and n are integers from 0 to 10; $R^1$ is hydrogen, halo, $C_1$-$C_4$-alkyl, $C_3$-$C_8$-cycloalkyl, phenyl, $C_5$-$C_8$-cycloalkenyl, naphthyl, indenyl, tetralinyl, decalinyl, adamantyl, a monocyclic heterocyclic ring system comprising 3 to 8 atoms in the ring or a bicyclic heterocyclic ring system comprising 6 to 11 atoms, provided that at least 1 atom of the ring system is carbon and at least 1 atom of the ring system is a heteroatom selected from O, N, and S; and wherein $R^1$ and the connecting alkyl groups -$(CH_2)_m$- and -$(CH_2)_n$- are optionally substituted by one or two halo, methyl, ethyl, methoxy, amino, N-protected-amino, methylamino, dimethylamino, acetoxy, acetamido, carbomethoxy, or hydroxyl groups, provided that, if the substituent is other than halo or alkyl, there can be no more than one substituent on any connecting —$CH_2$— group; X is O, S, —NH—, —N($CH_3$)—, —C≡C—, —CH=CH—, —C($CH_3$)=CH—, —CH=C($CH_3$)— or —C($CH_3$)=C($CH_3$)—;

$R^2$ is hydrogen, $C_1$-$C_{18}$-alkyl or $C_2$-$C_{18}$-alkenyl;

A is divalent oxygen, sulfur, sulfinyl or sulfonyl;

$A^1$ is divalent oxygen, sulfur, sulfinyl, sulfonyl or —NH—;

Y is hydrogen, chloro, bromo, iodo, nitro, $C_1$-$C_3$-alkyl; hydroxy, $C_1$-$C_3$-alkoxy, mercapto, $C_1$-$C_3$-alkylthio, carbamyl or $C_1$-$C_3$-alkylcarbamyl;

$Y^1$ is chloro, bromo or iodo, and $W^1$ is $C_1$-$C_{10}$-alkylene or $C_2$-$C_{10}$-alkenylene; provided that (1) if r=0, s must = 0; (2) the sum of the carbon atoms in the $R^2$ and W groups must be greater than 4, but cannot exceed 21; (3) when Y is mercapto, A and $A^1$ cannot be sulfinyl or sulfonyl; and (4) when A and $A^1$ are sulfinyl or sulfonyl, they must be in equal oxidation states. The salts of these compounds are also part of this invention.

A preferred subgroup of formula 1 compounds are those of group (b) wherein r and s=0, p=1, and $R^2$ is $C_5$-$C_{18}$ alkyl or $C_5$-$C_{18}$ alkenyl.

As used herein, the term "alkyl" or "alkenyl" comprehend both straight and branched hydrocarbon chains. By "alkenyl" is meant an unsaturated hydrocarbon group containing one, two, or three double bonds which may be either in the cis or trans configuration.

The term "$C_3$-$C_8$-cycloalkyl" means a saturated ring having from three to eight carbon atoms in the ring. Examples of such rings are cyclopropyl, cyclobutyl, cyclopentyl, cyclohexyl, and cyclooctyl. By "$C_5$-$C_8$-cycloalkenyl" is meant a carboxylic ring which contains from five to eight carbon atoms and which also contains one or two double bonds. Cyclohexadienyl, cyclohexenyl, cyclopentenyl, and cyclooctadienyl are examples of such rings.

The term "monocyclic or bicyclic heterocyclic ring system" as used herein includes saturated or unsaturated heterocyclic moieties containing at least one carbon atom and at least one heteroatom selected from oxygen, nitrogen and sulfur. Heterocyclic groups contemplated include:

unsaturated 3 to 8-membered monocyclic groups, for example, pyrrolyl, $\Delta^3$-pyrrolinyl, imidazolyl, pyrazolyl, pyridyl, pyrimidyl, pyrazinyl, pyridazinyl, triazinyl, triazolyl (e.g., 4H-1,2,4-triazolyl, 1H-1,2,3-triazolyl, etc.), tetrazolyl (e.g., 1H-tetrazolyl, 2H-tetrazolyl, etc.), oxazolyl, isoxazolyl, oxadiazolyl (e.g., 1,2,4-oxadiazolyl, 1,3,4-oxadiazolyl, 1,2,5-oxadiazolyl, etc.), thiazolyl, isothiazolyl, thiadiazolyl (e.g., 1,2,4-thiadiazolyl, 1,3,4-thiadiazolyl, 1,2,5-thiadiazolyl, etc.), thienyl, furanyl, etc.;

saturated 3 to 8-membered monocyclic groups, for example, pyrrolidinyl, imidazolidinyl, piperidinyl, piperazinyl, morpholinyl, thiazolidinyl, tetrahydrofuranyl, tetrahydrothienyl, tetrahydropyranyl, dioxanyl, etc.;

unsaturated 6 to 11-membered bicyclic groups, for example, indolyl, isoindolyl, benzothiofuranyl, benzimidazolyl, quinolyl, isoquinolyl, cinnolinyl, quinazolinyl, etc.; and the like.

"N-protected-amino" means that the amino group is substituted by a suitable protecting group. Such a group must be one which is compatible with the other functional groups in the compound and which can be readily removed under acidic conditions. One especially suitable amino-protecting group is the tert-butoxycarbonyl (t-BOC) group.

When R is a group (a) moiety and X is —CH=CH—, —C(CH$_3$)=CH—, —CH=C(CH$_3$)—, or —C(CH$_3$)=C(CH$_3$)—, the R group can be in either the cis or trans configuration.

Illustrative acyl groups include those wherein:
(1) R is

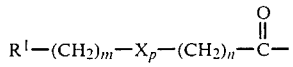

and
(a) R$^1$ is hydrogen or C$_1$-C$_4$-alkyl;
(b) p is 0;
(c) R$^1$ is optionally substituted phenyl;
(d) X is oxygen or —NH— and n is 0; or
(e) X is oxygen or sulfur and n is 1; and
(2) R is R$^3$—SO$_2$ and
(a) R$^3$ is C$_1$-C$_5$-alkyl; or
(b) R$^3$ is optionally substituted phenyl.

The compounds of this invention are prepared by acylating the amino group on the peptide nucleus of the glycopeptide antibiotic by treatment with acylating agents using methods known in the art for forming an amide bond. The acylation is accomplished, in general, by reacting the parent antibiotic with an activated derivative of the substituted compound of formulas 3 (a), (b) or (c) corresponding to the desired acyl side chain group (R).

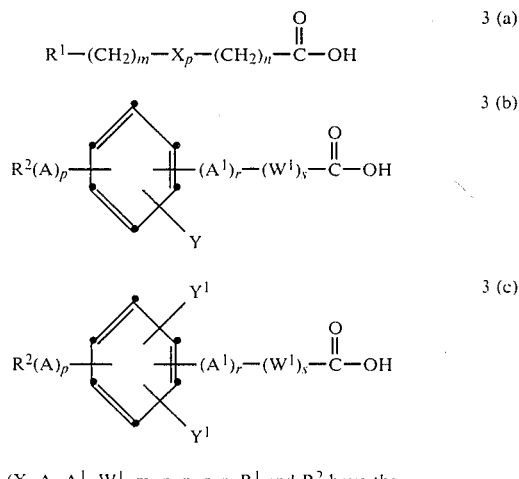

(X, A, A$^1$, W$^1$, m, n, p, r, s, R$^1$ and R$^2$ have the meanings herein described supra.)

By the term "activated derivative" is meant a derivative which renders the carboxyl function of the acylating agent reactive to coupling with the primary amino group to form the amide bond which links the acyl group to the parent antibiotic. Suitable activated derivatives, their methods of preparation, and their methods of use as acylating agents for a primary amine will be recognized by those skilled in the art. Preferred activated derivatives are: (a) an acid halide (e.g. acid chloride), (b) an acid anhydride (e.g. an alkoxyformic acid anhydride or aryloxyformic acid anhydride) or (c) an activated ester (e.g. a 2,4,5-trichlorophenyl ester, an N-hydroxybenztriazole ester, or an N-hydroxysuccinimide ester). Other methods for activating the carboxyl function include reaction of the carboxylic acid with a carbonyldiimide (e.g. N,N'-dicyclohexylcarbodiimide or N,N'-diisopropylcarbodiimide) to give a reactive intermediate which, because of instability, is not isolated, the reaction with the primary amine being carried out in situ.

A preferred method for preparing the compounds of formula 1 is by the active ester method. The use of the 2,4,5-trichlorophenyl ester of the desired side chain acid (formula 3) as the acylating agent is most preferred. In this method, an excess amount of the active ester is reacted with the antibiotic at room temperature in a non-reactive organic solvent such as dimethylformamide (DMF). The reaction time is not critical, although a time of about 24 to about 120 hours is preferred. At the conclusion of the reaction, the solvent is removed, and the residue is purified by chromatography, such as over reversed phase HPLC using silica gel C$_{18}$ reversed phase resin as the stationary phase.

The 2,4,5-trichlorophenyl esters are conveniently made by treating the side chain acid (formula 3) with 2,4,5-trichlorophenol in the presence of a coupling agent, such as N,N'-dicyclohexylcarbodiimide. Other methods of preparation of the active esters will be apparent to those skilled in the art.

The substituted acids of formula 3, and the activated derivatives thereof, are either known compounds or they can be made from known compounds by methods known in the art.

The parent antibiotics used as starting materials in the process of this invention are all members of the group of glycopeptide antibiotics. Antibiotic A35512 factors A, B, C, E and H are described by Karl H. Michel and Calvin E. Higgens in U.S. Pat. No. 4,122,168, issued Oct. 24, 1978; and A35512B pseudo (ψ)aglycone is described by Manuel Debono in U.S. Pat. No. 4,029,769, issued June 14, 1977 (note: in the patent, this compound is called A35512B aglycone, but will be called A35512B ψaglycone herein since it retains the amino-sugar). Actaplanin (antibiotic A-4696) factors A and B are described by Hamill et al. in U.S. Pat. No. 4,115,552, issued Sept. 19, 1978. Actaplanin factors B$_1$, B$_2$, B$_3$, C$_{1a}$, C$_3$ and E$_1$ are described by Debono et al. in U.S. Pat. No. 4,322,406, issued Mar. 30, 1982. The actaplanin pseudo-aglycone is described by Debono in U.S. Pat. No. 4,029,769, issued Mar. 30, 1982. Actaplanin factor G is described by Hershberger et al. in U.S. Pat. No. 4,461,723, issued July 24, 1984; and actaplanin factors K, L, M, N and O are described by Hunt et al. in an allowed co-pending application, Ser. No. 488,967, filed Apr. 27, 1983. A41030 factors A, B, C, D, E, F and G are described in the co-pending application of Michel et al., Ser. No. 443,496, filed Nov. 22, 1982; and A47934 is described by Hamill et al. in U.S. Pat. No. 4,462,942, issued July 31, 1984. Ristocetin A preparation is described by Philip et al. in U.S. Pat. No. 2,990,329, issued June 27, 1961. Ristocetin ψaglycone is prepared as described by Williams et al. in J.C.S. Chem. Comm. 1979, 906–908 (see esp. p. 907).

The structures of A35512B and its ψaglycone are shown in formulas 4a and 4b:

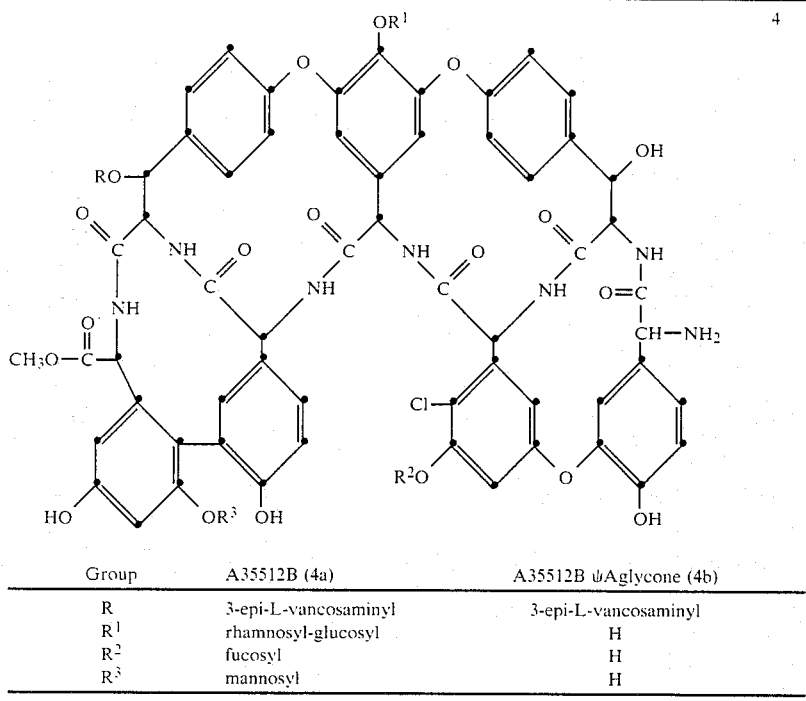

| Group | A35512B (4a) | A35512B ψAglycone (4b) |
|---|---|---|
| R | 3-epi-L-vancosaminyl | 3-epi-L-vancosaminyl |
| $R^1$ | rhamnosyl-glucosyl | H |
| $R^2$ | fucosyl | H |
| $R^3$ | mannosyl | H |

Thus, the new A35512B derivatives of this invention have formulas 5a and 5b:

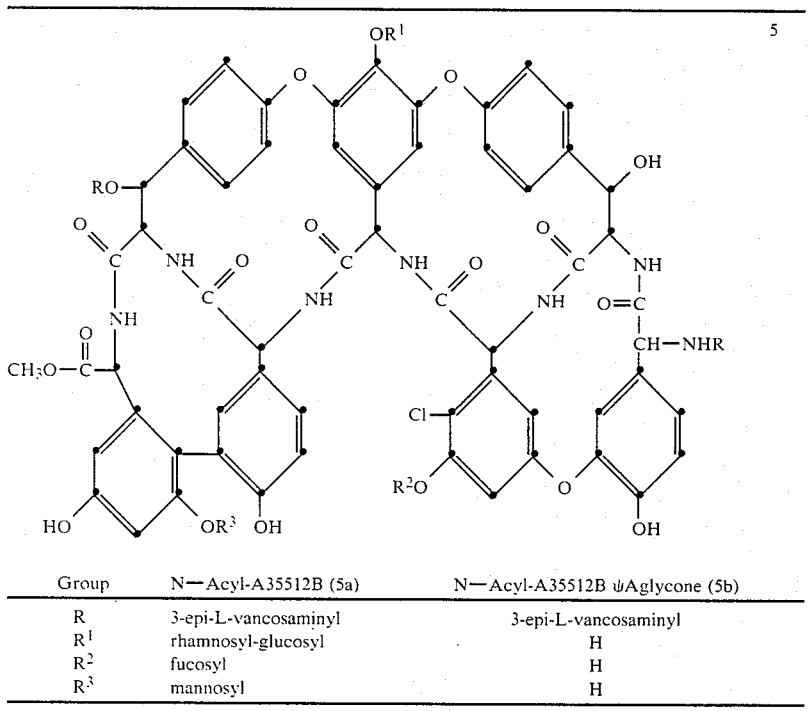

| Group | N—Acyl-A35512B (5a) | N—Acyl-A35512B ψAglycone (5b) |
|---|---|---|
| R | 3-epi-L-vancosaminyl | 3-epi-L-vancosaminyl |
| $R^1$ | rhamnosyl-glucosyl | H |
| $R^2$ | fucosyl | H |
| $R^3$ | mannosyl | H |

The remaining A35512 factors A, C, E and H have not been completely characterized, but each contains the

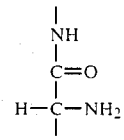

moiety and each will, therefore, react in a similar manner to form the corresponding

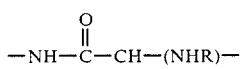

containing products.

The structure of ristocetin A and its pseudoaglycone are shown in formulas 6a and 6b:

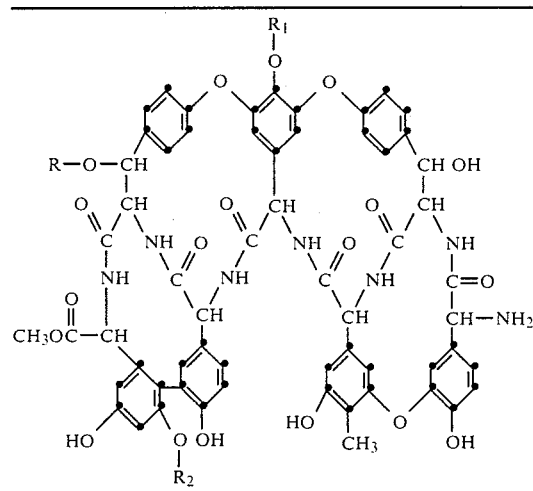

| Group | Ristocetin A (6a) | Ristocetin A ψAglycone (6b) |
|---|---|---|
| R | ristosaminyl | ristosaminyl |
| $R_1$ | O—β-D-arabinopyranosyl- | H |
| | (1→2)-O—α-D-mannopyranosyl- | |
| | (1→2)-O—α-L-rhamnopyranosyl- | |
| | (1→6)-O—β-D-glucopyranosyl | |
| $R_2$ | mannosyl | H |

Thus, the new ristocetin A derivatives of this invention have formulas 7a and 7b:

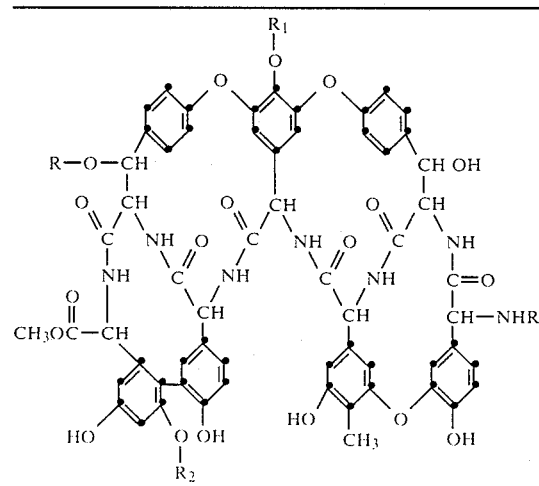

N—Acyl-Ristocetin    N—Acyl-Ristocetin Pseudo-

| Group | (7a) | aglycone (7b) |
|---|---|---|
| R | ristosaminyl | ristosaminyl |
| $R_1$ | O—β-D-arabinopyranosyl- | H |
| | (1→2)-O—α-D-mannopyranosyl- | |
| | (1→2)-O—α-L-rhamnopyranosyl- | |
| | (1→6)-O—β-D-glucopyranosyl | |
| $R_2$ | mannosyl | H |

The structure of A47934 is shown in formula 8:

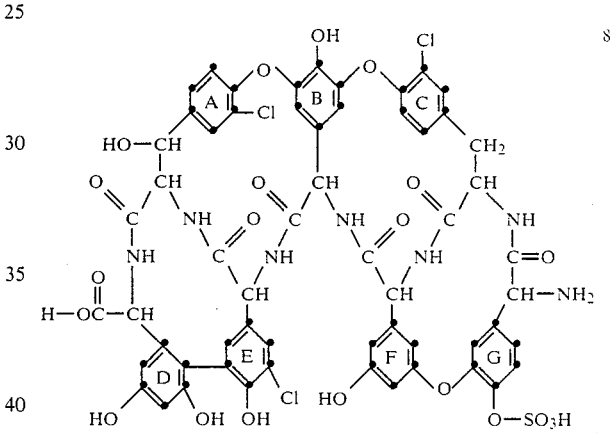

Thus, the new A47934 derivative of this invention has formula 9:

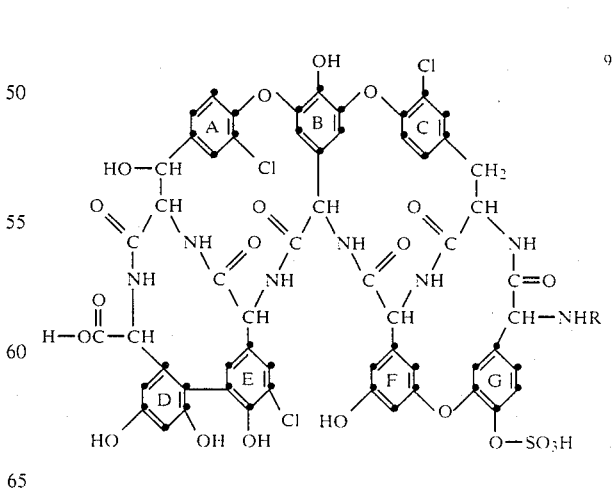

The structures of A41030 factors A, B, C, D, E and F are shown in formulas 10a–10g.

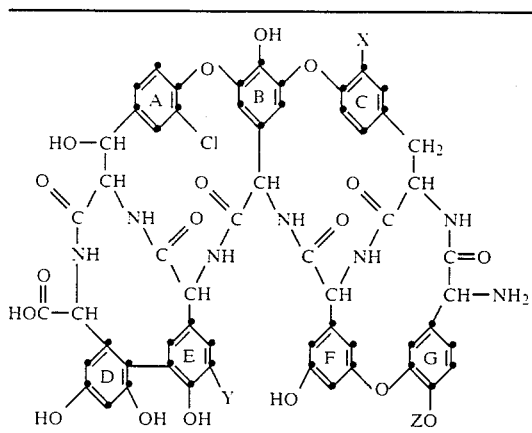

| Formula | A41030 | X | Y | Z |
|---|---|---|---|---|
| 10a | A | Cl | Cl | H |
| 10b | B | Cl | H | H |
| 10c | C | Cl | Cl | galactosyl |
| 10d | D[a] | H | Cl | H |
| 10e | E | H | H | H |
| 10f | F | Cl | Cl | galactosyl-galactosyl |
| 10g | G[a] | Cl | Cl | galactosyl-galactosyl |

[a]Factors D and G have two equivalent n-butyl groups attached to the peptide nucleus at an undetermined location.

Thus, the new A41030 derivatives of this invention have formulas 11a–11g:

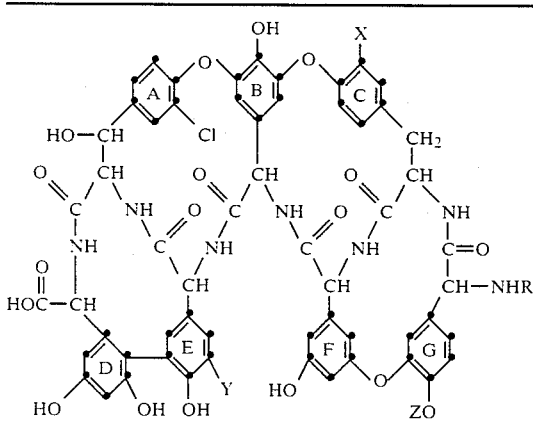

| Formula | N—Acyl-A41030 Factors | X | Y | Z |
|---|---|---|---|---|
| 11a | A | Bl | Cl | H |
| 11b | B | Cl | H | H |
| 11c | C | Cl | Cl | galactosyl |
| 11d | D[a] | H | Cl | H |
| 11e | E | H | H | H |
| 11f | F | Cl | Cl | galactosyl-galactosyl |
| 11g | G[a] | Cl | Cl | galactosyl-galactosyl |

[a]See footnote to formulas 11 and 11

The actaplanin factors and pseudoaglycone have the structures shown in formulas 12a–12p:

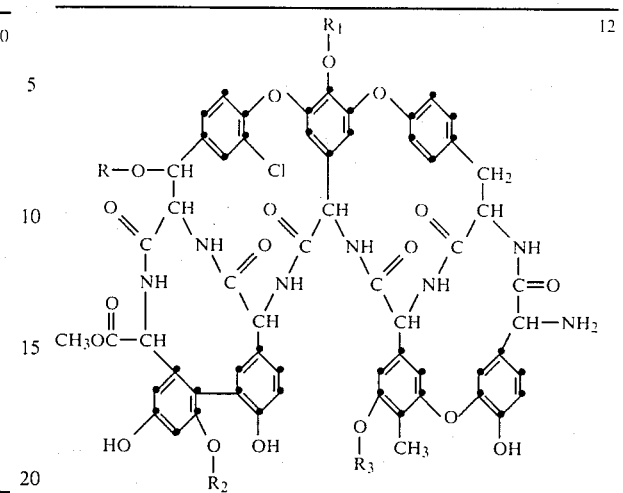

| Formula | Actaplanin | $R_1$ | $R_2$ | $R_3$ |
|---|---|---|---|---|
| 12a | A | mannosyl-glucosyl | mannosyl | mannosyl |
| 12b | $B_1$ | rhamnosyl-glucosyl | mannosyl | mannosyl |
| 12c | $B_2$ | glycosyl | mannosyl | mannosyl |
| 12d | $B_3$ | mannosyl-glucosyl | mannosyl | H |
| 12e | $C_{1a}$ | rhamnosyl-glucosyl | manosyl | H |
| 12f | $C_{2a}$ | H | mannosyl | mannosyl |
| 12g | $C_3$ | glucosyl | H | mannosyl |
| 12h | $D_1$ | H | mannosyl | H |
| 12i | $D_2$ | H | H | mannosyl |
| 12j | G | glucosyl | mannosyl | H |
| 12k | K | mannosyl-glucosyl | H | mannosyl |
| 12m | L | rhamnosyl-glucosyl | H | mannosyl |
| 12n | M | mannosyl-glucosyl | H | H |
| 12o | N | rhamnosyl-glucosyl | H | H |
| 12p | O | glucosyl | H | H |
| 12q | ψaglycone | H | H | H |

Thus, the actaplanin derivatives prepared by the process of this invention have formulae 13a–13p.

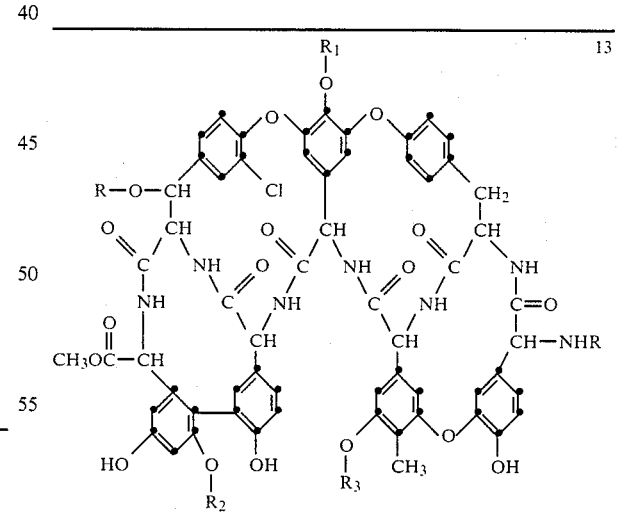

| Formula | N—Acyl-Actaplanin Factors | $R_1$ | $R_2$ | $R_3$ |
|---|---|---|---|---|
| 13a | A | mannosyl-glucosyl | mannosyl | mannosyl |
| 13b | $B_1$ | rhamnosyl-glucosyl | mannosyl | mannosyl |
| 13c | $B_2$ | glucosyl | mannosyl | mannosyl |
| 13d | $B_3$ | mannosyl-glucosyl | mannosyl | H |
| 13e | $C_{1a}$ | rhamnosyl-glucosyl | manosyl | H |
| 13f | $C_{2a}$ | H | mannosyl | mannosyl |
| 13g | $C_3$ | glucosyl | H | mannosyl |

-continued

| | | | | |
|---|---|---|---|---|
| 13h | D₁ | H | mannosyl | H |
| 13i | D₂ | H | H | mannosyl |
| 13j | G | glucosyl | mannosyl | H |
| 13k | K | mannosyl-glucosyl | H | mannosyl |
| 13m | L | rhamnosyl-glucosyl | H | mannosyl |
| 13n | M | mannosyl-glucosyl | H | H |
| 13o | N | rhamnosyl-glucosyl | H | H |
| 13p | O | glucosyl | H | H |
| 13q | ψaglycone | H | H | H |

The derivatives of this invention inhibit the growth of pathogenic bacteria, especially gram-positive bacteria. The minimal inhibitory concentrations (MIC's) at which illustrative compounds inhibit certain bacteria are given in Table I. The MIC's in Table I were determined by standard agar-dilution assays.

TABLE I

Antibiotic Activity of Formula 1 Compounds[a]

| Test Organism | Test Compound[b] | | | | | | | | | | | | | | |
|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 |
| Staphylococcus aureus X1.1 | 8 | 4 | 4 | 4 | 4 | 2 | 4 | 2 | 4 | 4 | 8 | 4 | 2 | 8 | 1 |
| Staphylococcus aureus V41[c] | 8 | 4 | 8 | 8 | 4 | 4 | 4 | 2 | 8 | 4 | 4 | 8 | 2 | 8 | 1 |
| Staphylococcus aureus X400[d] | 16 | 8 | 8 | 16 | 4 | 4 | 8 | 2 | 8 | 8 | 8 | 16 | 2 | 8 | 1 |
| Staphylococcus aureus S13E | 8 | 4 | 4 | 8 | 8 | 4 | 4 | 2 | 8 | 4 | 8 | 8 | 2 | 8 | 1 |
| Staphylococcus epidermidis EPI1 | 8 | 4 | 8 | 8 | 4 | 8 | 8 | 2 | 16 | 4 | 4 | 8 | 2 | 4 | 2 |
| Staphylococcus epidermidis EPI2 | 32 | 8 | 8 | 16 | 8 | 8 | 16 | 4 | 16 | 16 | 16 | 16 | 4 | 16 | 2 |
| Streptococcus pyogenes C203 | 1 | 2 | 1 | 2 | 2 | 1 | 2 | 2 | 2 | 2 | 1 | 2 | 2 | 4 | 1 |
| Streptococcus pneumoniae Park I | 2 | 4 | 1 | 2 | 4 | 1 | 4 | 4 | 2 | 4 | 1 | 2 | 4 | 4 | — |
| Streptococcus Group D X66 | 4 | 4 | 4 | 8 | 8 | 2 | 4 | 4 | 8 | 4 | 8 | 4 | 4 | 2 |
| Streptococcus Group 9960 | 2 | 4 | 2 | 4 | 4 | 4 | 4 | 2 | 4 | 8 | 2 | 8 | 2 | 8 | 2 |
| Haemophilus influenzae C.L.[e] | NT[g] | NT | NT | —[h] | NT | NT | — | NT | NT | — | — | NT | — | — | — |
| Haemophilus influenzae 76[f] | NT | NT | NT | — | NT | NT | — | NT | NT | — | — | NT | — | — | — |

| Test Organism | Test Compound[b] | | | | | | | | | | |
|---|---|---|---|---|---|---|---|---|---|---|---|
| | 16 | 17 | 18 | 19 | 20 | 21 | 22 | 23 | 24 | 25 | 26 |
| Staphylococcus aureus X1.1 | 0.25 | 0.125 | 0.25 | 0.125 | 0.5 | 1 | 0.125 | 0.125 | 0.06 | 0.125 | 0.125 |
| Staphylococcus aureus V41[c] | 0.25 | 0.125 | 0.5 | 0.25 | 0.5 | 1 | 0.125 | 0.125 | 0.06 | 0.125 | 0.25 |
| Staphylococcus aureus X400[d] | 0.5 | 0.125 | 0.5 | 0.25 | 1 | 2 | 0.25 | 0.25 | 0.25 | 0.25 | 0.5 |
| Staphylococcus aureus S13E | 0.25 | 0.125 | 0.25 | 0.25 | 0.5 | 2 | 0.25 | 0.125 | 0.06 | 0.125 | 0.25 |
| Staphylococcus epidermidis EPI1 | 0.25 | 0.125 | 0.25 | 0.125 | 0.5 | 0.5 | 0.125 | 0.125 | 0.125 | 0.06 | 0.125 |
| Staphylococcus epidermidis EPI2 | 0.5 | 0.125 | 0.5 | 0.25 | 0.5 | 1 | 0.25 | 0.5 | 0.25 | 0.125 | 0.5 |
| Streptococcus pyogenes C203 | 0.5 | 0.125 | 1 | 0.5 | 1 | 2 | 0.5 | 0.5 | 0.25 | 0.5 | 0.5 |
| Streptococcus pneumoniae Park I | 0.5 | 0.125 | 0.5 | 0.5 | 1 | 2 | 0.5 | 0.125 | 0.06 | 0.25 | 0.5 |
| Streptococcus Group D X66 | 1 | 0.5 | 1 | 0.25 | 0.5 | 2 | 0.5 | 1 | 0.5 | 0.25 | 0.5 |
| Streptococcus Group 9960 | 0.125 | 0.125 | 2 | 0.25 | 0.5 | 1 | 0.5 | 2 | 1 | 0.25 | 1 |
| Haemophilus influenzae C.L.[e] | 32 | 8 | — | 32 | 32 | — | 16 | 8 | 4 | 8 | 8 |
| Haemophilus influenzae 76[f] | 32 | 16 | 64 | 16 | 32 | — | 8 | 8 | 4 | 8 | 4 |

[a]MIC in mcg/ml
[b]Compound numbers = Example nos.
[c]Penicillin-resistant strain
[d]Methicillin-resistant strain
[e]Ampicillin-sensitive strain
[f]Ampicillin-resistant strain
[g]NT = not tested
[h]Compound not active at less than 128 mcg/ml Some of the derivatives of this invention have shown in vivo antimicrobial activity against experimentally-induced infections in laboratory animals. When two doses of test compound were administered to experimentally infected mice, the activity observed was measured as an $ED_{50}$ value [effective dose in mg/kg to protect 50% of the test animals: see Warren Wick, et al., J. Bacteriol. 81, 233-235 (1961)]. $ED_{50}$ values observed for illustrative compounds are given in Table II.

TABLE II $ED_{50}$ Values of Formula 1 Compounds in Mice[a]

| Test Compound | Staphylococcus aureus | Streptococcus pyogenes | Streptococcus pneumoniae |
|---|---|---|---|
| 2 | 5.87 | —[c] | — |
| 3 | 10.84 | — | — |
| 5 | 14.4 | — | — |
| 7 | 4.5 | — | — |
| 8 | 11.34 | — | — |
| 9 | 70 | — | — |
| 10 | 5.7 | — | — |
| 11 | 11.8 | — | — |
| 12 | 10.97 | — | — |
| 17 | 0.08 | >10 | 8.52 |
| 18 | 0.46 | >10 | >10 |
| 19 | <0.31 | >10 | >10 |
| 20 | 0.6 | >10 | >10 |
| 21 | 2.19 | >10 | >10 |
| 22 | <0.31 | >10 | 41 |
| 24 | <0.31 | — | — |
| 25 | <0.31 | >10 | >10 |
| 26 | 3.6 | >10 | >10 |

[a]mg/kg × 2; administered subcutaneously 1 and 4 hours post-infection
[b]Compound numbers = example numbers
[c]Not tested This invention also relates to a method of controlling bacterial infections. In carrying out the method of this invention, an effective amount of a compound of formula 1 is administered parenterally or orally or an infected or susceptible warm-blooded animal. The compound can also be administered by insufflation, i.e. by blowing the compound, in the form of a medicated dust, into an enclosed space or room wherein the animals or poultry are held. The animals or poultry breathe the medicated dust present in the air; the medicated dust is also taken into the body through the eyes (a process called intraocular injection).

The dose which is effective to control the infection will vary with the severity of the infection and the age, weight, and condition of the animal. The total dose required for protection parenterally will generally, however, be in the range of from about 0.1 to about 100 mg/kg and preferably will be in the range of from about 0.5 to about 50 mg/kg. The dose required for oral administration will generally be in the range of from 1 to about 300 mg/kg and preferably will be in the range of from about 1 to about 100 mg/kg. Suitable dosage regiments can be constructed.

In another aspect, this invention relates to compositions useful for the control of bacterial infections. These compositions comprise a compound of formula 1 together with a suitable vehicle. Compositions may be formulated for parenteral or oral administration by methods recognized in the pharmaceutical art.

Effective injectable compositions containing these compounds may be in either suspension or solution form. In the preparation of suitable formulations it will be recognized that, in general, the water solubility of the acid addition salts is greater than that of the free bases. Similarly, the bases are more soluble in dilute acids or in acidic solutions than in neutral or basic solutions.

In the solution form the compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate. Such aqueous solutions contain, in general, no more than 50% of the organic solvent by volume.

Injectable suspension compositions require a liquid suspending medium, with or without adjuvants, as a vehicle. The suspending medium can be, for example, aqueous polyvinylpyrrolidone, inert oils such as vegetable oils or highly refined mineral oils, or aqueous carboxymethylcellulose.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents.

Many substances which affect the hydrophilicity, density, and surface tension of the liquid suspending medium can assist in making injectable suspensions in individual cases. For example, silicone antiforms, sorbitol, and sugars can be useful suspending agents.

In another embodiment, this invention relates to methods of increasing feed-utilization efficiency and promoting growth rates in animals such as poultry, swine, sheep and cattle and of enhancing milk production in ruminants. For increasing feed-utilization efficiency and promoting growth, a formula 1 compound is administered orally in a suitable feed in an amount of from about 2 to about 200 grams per ton of total feed. For enhancing milk production in ruminants, oral administration of a daily amount of from about 0.1 to about 10 mg/kg of body weight (or about 100 to about 600 mg/ruminant/day) is suggested. The formula 1 compounds wherein W is the remaining portion of an actaplanin factor are especially preferred for this embodiment.

Often the most practical way to administer the compounds is by formulation into the feed supply or drinking water. A variety of feeds, including the common dry feeds, liquid feeds, and pelleted feeds, may be used.

The methods of formulating drugs into animal feeds are well-known. A preferred method is to make a concentrated-drug premix which in turn is used to prepare medicated feeds. Typical premixes may contain from about 1 to about 200 grams of drug per pound of premix. Premixes may be either liquid or solid preparations.

The final formulation of feeds for animals of poultry will depend upon the amount of drug to be administered. The common methods of formulating, mixing, and pelleting feeds may be used to prepare feeds containing a compound of formula 1.

The following examples are provided to illustrate this invention:

EXAMPLE 1

Preparation of N-[N-(tert-butoxycarbonyl)-L-phenylalanyl]-A35512B

N-(tert-Butoxycarbonyl)-L-phenylalanine (500 mg, 1.12 mmoles) was added to a solution of A35512B free base (2 g, 1.02 mmoles) in anhydrous DMF (100 ml). The reaction mixture was stirred at room temperature under nitrogen for 18 hours and then was concentrated under vacuum to near dryness. The resulting viscous oil was diluted with diethyl ether (200 ml). The creamy white precipitate which formed was separated by filtration and dried to give 2.62 g of crude product. A portion of the crude product (450 mg) was chromatographed over a reversed-phase $C_{18}$ silica-gel column (Water's Prep 500), eluting with a water:methanol:acetonitrile (3:1:1) containing 0.1% pyridinium acetate (pH5) solvent system. Fractions containing the product were located by TLC, combined and lyophilized to give 285 mg of the title compound. (67% yield).

EXAMPLE 2

Preparation of N-(L-phenylalanyl)A35512B

N-[N-(t-Boc)-L-phenylalanyl]A35512B (400 mg), prepared as described in Example 1, was dissolved in 5 ml of trifluoroacetic acid (TFA) containing 1% anisole. The reaction mixture was stirred for 10 minutes at room temperature under nitrogen. The reaction mixture was concentrated, and the TFA salt was collected by trituration with diethyl ether (100 ml) and filtering. The TFA salt was dissolved in water (20 ml); the pH of this solution was adjusted to 6.8 with pyridine; and the solution was lyophilized to give 368 mg of the title compound as a white solid (m.w. 2098, 96% yield)

EXAMPLES 3-26

Using the procedure of Example 1 and, where applicable, that of Example 2, and the appropriate starting materials, the following compounds were prepared:

| Example No. | Compound |
| --- | --- |
| 3 | N—[N—(hexanoyl)-L-tryptophyl]A35512B |
| 4 | N—[N—(t-Boc)—D-phenylglycyl]A35512B |
| 5 | N—(D-phenylglycyl)A35512B |
| 6 | N—[N—(t-Boc)—11-aminoundecanoyl]A35512B |
| 7 | N—(11-aminoundecanoyl)A35512B |
| 8 | N—(nonanoyl)A35512B |
| 9 | N—[p-(dodecyloxy)phenylpropanoyl]A35512B |

-continued

| Example No. | Compound |
|---|---|
| 10 | N—[(1-tetrazole)acetyl]A35512B |
| 11 | N—(3,5-dichlorobenzoyl)A35512B |
| 12 | N—[(3-sydnone)acetyl]A35512B |
| 13 | N—(nonanoyl)A35512B pseudoaglycone |
| 14 | N—[N—(t-Boc)—11-aminoundecanoyl]A35512B pseudoaglycone |
| 15 | N—(11-aminoundecanoyl)A35512B pseudoaglycone |
| 16 | N—[N—(t-Boc)—L-phenylalanyl]A41030A |
| 17 | N—(L-phenylalanyl)A41030A |
| 18 | N—[4-(N,N—dimethylamino)benzoyl]A41030A |
| 19 | N—(nonanoyl)A41030A |
| 20 | N—(lauroyl)A41030A |
| 21 | N—[p-(octyloxy)benzoyl]A41030A |
| 22 | N—(3,5-dichlorobenzoyl)A41030A |
| 23 | N—[N—(t-Boc)—L-phenylalanyl]A47934 |
| 24 | N—(L-phenylalanyl)A47934 |
| 25 | N—(nonanoyl)A47934 |
| 26 | N—[p-(octyloxy)benzoyl]A47934 |

EXAMPLES 27-40

Using the procedure of Example 1 and, where applicable, that of Example 2, and the appropriate starting materials, the following compounds can be prepared:

| Example No. | Compound |
|---|---|
| 27 | N—(benzoyl)actaplanin factor A |
| 28 | N—(decanoyl)ristocetin A |
| 29 | N—(acetyl)actaplanin pseudoaglycone |
| 30 | N—[(quinolin-1-yl)acetyl]A35512 factor H |
| 31 | N—[3-(cyclohexyl)propionyl]A41030 factor D |
| 32 | N—(L-phenylalanyl)A35512 factor A |
| 33 | N—(butanoyl)actaplanin factor G |
| 34 | N—(L-phenylalanyl)ristocetin A |
| 35 | N—[(pyridin-2-yl)acetyl]actaplanin factor $C_{1a}$ |
| 36 | N—[N-(t-butanoyl)-L-tryptophyl]ristocetin A |
| 37 | N—(11 aminoundecanoyl)ristocetin A pseudoaglycone |
| 38 | N—[(thien-2-yl)acetyl]actaplanin factor A |
| 39 | N—[(phenyl)acetyl]A41030 factor F |
| 40 | N—[3-(phenyl)propionyl]A47934 |

I claim:

1. A compound of the formula

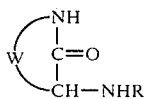

wherein W is the remaining portion of a glycopeptide antibiotic selected from A35512 factors A, B, C, E and H, A35512B pseudoaglycone, A41030 factors A, B, C, D, E, F and G, A47934, ristocetin A, ristocetin A pseudoaglycone, actaplanin factors A, $B_1$, $B_2$, $B_3$, $C_{1a}$, $C_{2a}$, $C_3$, $D_1$, $D_2$, $E_1$, G, K, L, M, N and O and actaplanin pseudoaglycone which have the common formula:

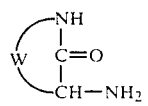

and R is an acyl group selected from:

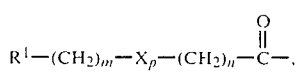

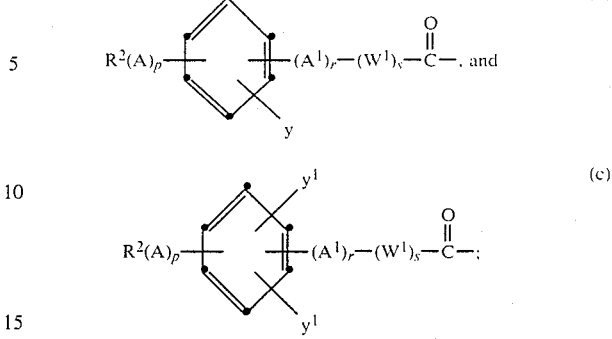

p, r, and s are 0 or 1; m and n are integers from 0 to 10; $R^1$ is hydrogen, halo, $C_1$-$C_4$-alkyl, $C_3$-$C_8$-cycloalkyl, phenyl, $C_5$-$C_8$-cycloalkenyl, naphthyl, indenyl, tetralinyl, decalinyl, adamantyl, a monocyclic heterocyclic ring system comprising 3 to 8 atoms in the ring or a bicyclic heterocyclic ring system comprising 6 to 11 atoms, provided that at least 1 atom of the ring system is carbon and at least 1 atom of the ring system is a heteroatom selected from O, N, and S; and wherein $R^1$ and the connecting alkyl groups —$(CH_2)_m$— and —$(CH_2)_n$— are optionally substituted by one or two halo, methyl, ethyl, methoxy, amino, N-protected-amino, methylamino, dimethylamino, acetoxy, acetamido, carbomethoxy, or hydroxyl groups, provided that, if the substituent is other than halo or alkyl, there can be no more than one substituent on any connecting —$CH_2$— group; X is O, S, —NH—, —N($CH_3$)—, —C≡C—, —CH=CH—, —C($CH_3$)=CH—, —CH=C($CH_3$)— or —C($CH_3$)=C($CH_3$)—;

$R^2$ is hydrogen, $C_1$-$C_{18}$-alkyl or $C_2$-$C_{18}$-alkenyl;

A is divalent oxygen, sulfur, sulfinyl or sulfonyl;

$A^1$ is divalent oxygen, sulfur, sulfinyl, sulfonyl or —NH—;

Y is hydrogen, chloro, bromo, iodo, nitro, $C_1$-$C_3$-alkyl, hydroxy, $C_1$-$C_3$-alkoxy, mercapto, $C_1$-$C_3$-alkylthio, carbamyl or $C_1$-$C_3$-alkylcarbamyl;

$Y^1$ is chloro, bromo or iodo; and $W^1$ is $C_1$-$C_{10}$-alkylene or $C_2$-$C_{10}$-alkenylene; provided that (1) if r=0, s must=0; (2) the sum of the carbon atoms in the $R^2$ and W groups must be greater than 4, but cannot exceed 21; (3) when Y is mercapto, A and $A^1$ cannot be sulfinyl or sulfonyl; and (4) when A and $A^1$ are sulfinyl or sulfonyl, they must be in equal oxidation states; and its salts.

2. A compound of claim 1 wherein R is a group (b) moiety r and s=0, p=1, and $R^2$ is $C_5$-$C_{18}$ alkyl or $C_5$-$C_{18}$ alkenyl.

3. A compound of claim 1 wherein the glycopeptide is selected from A35512 factors A, B, C, E and H and A35512B pseudoaglycone.

4. A compound of claim 1 wherein the glycopeptide is selected from A41030 factors A, B, C, D, E, F and G.

5. A compound of claim 1 wherein the glycopeptide is selected from A47934.

6. A compound of claim 1 wherein the glycopeptide is selected from ristocetin A and ristocetin A pseudoaglycone.

7. The compound of claim 1 which is N-(L-phenylalanyl)A35512B.

8. The compound of claim 1 which is N-[N-(hexanoyl)-L-tryptophyl]A35512B.

9. The compound of claim 1 which is N-[N-(t-BOC)-D-phenylglycyl]A35512B.

10. The compound of claim 1 which is N-(D-phenylglycyl)A35512B.

11. The compound of claim 1 which is N-[N-(t-BOC)-11-aminoundecanoyl]A35512B.

12. The compound of claim 1 which is N-(11-aminoundecanoyl)A35512B.

13. The compound of claim 1 which is N-(nonanoyl)A35512B.

14. The compound of claim 1 which is N-[p-(dodecyloxy)phenylpropanoyl]A35512B.

15. The compound of claim 1 which is N-[(1-tetrazole)acetyl]A35512B.

16. The compound of claim 1 which is N-(3,5-dichlorobenzoyl)A35512B.

17. The compound of claim 1 which is N-[(3-sydnone)acetyl]A35512B.

18. The compound of claim 1 which is N-(nonanoyl)A35512B pseudoaglycone.

19. The compound of claim 1 which is N-[N-(t-Boc)-11-aminoundecanoyl]A35512B pseudoaglycone.

20. The compound of claim 1 which is N-(11-aminoundecanoyl)A35512B pseudoaglycone.

21. The compound of claim 1 which is N-[N-(t-Boc)-L-phenylalanyl]A41030A.

22. The compound of claim 1 which is N-(L-phenylalanyl)A41030A.

23. The compound of claim 1 which is N-[4-(N,N-dimethylamino)benzoyl]A41030A.

24. The compound of claim 1 which is N-(nonanoyl)A41030A.

25. The compound of claim 1 which is N-(lauroyl)A41030A.

26. The compound of claim 1 which is N-[p-(octyloxty)benzoyl]A41030A.

27. The compound of claim 1 which is N-(3,5-dichlorobenzoyl)A41030A.

28. The compound of claim 1 which is N-[N-(t-Boc)-L-phenylalanyl]A47934.

29. The compound of claim 1 which is N-(L-phenylalanyl)A47934.

30. The compound of claim 1 which is N-(nonanoyl)A47934.

31. The compound of claim 1 which is N-[p-(octyloxy)benzoyl]A47934.

32. A pharmaceutical composition for treating gram-positive bacterial infections which comprises an effective amount of a compound of claim 1, or a pharmaceutically acceptable salt thereof, and a suitable pharmaceutical vehicle.

33. A method of treating susceptible gram-positive bacterial infections which comprises administering an effective amount of a composition of claim 32 to an infected or susceptible warm-blooded animal.

34. A feed composition for increasing feed-utilization efficiency in animals which comprises (1) an effective amount of a compound of claim 1, or a pharmaceutically-acceptable salt thereof, and (2) a standard feed ration.

35. A method for increasing feed-utilization in animals which comprises administering an effective amount of a composition of claim 34 to the animal.

36. A feed composition for improving milk production in lactating ruminants comprising (1) an effective amount of a compound of claim 1, or a pharmaceutically acceptable salt thereof, and (2) a standard feed ration.

37. A method for improving milk production in lactating ruminants comprising orally administering an effective amount of a composition of claim 36 to the ruminant.

38. The method of claim 37 wherein the ruminant is a dairy cow.

* * * * *